US009089530B2

(12) United States Patent
Tanaka et al.

(10) Patent No.: US 9,089,530 B2
(45) Date of Patent: Jul. 28, 2015

(54) ANTIMALARIAL DRUG WHICH CONTAINS 5-AMINOLEVULINIC ACID OR DERIVATIVE THEREOF AS ACTIVE INGREDIENT

(75) Inventors: Tohru Tanaka, Tokyo (JP); Satofumi Kawata, Tokyo (JP); Takeo Kohda, Tokyo (JP); Motowo Nakajima, Tokyo (JP); Kiyoshi Kita, Tokyo (JP)

(73) Assignees: SBI Pharmaceuticals Co., Ltd., Tokyo (JP); The University of Tokyo, Tokyo (JP)

( * ) Notice: Subject to any disclaimer, the term of this patent is extended or adjusted under 35 U.S.C. 154(b) by 107 days.

(21) Appl. No.: 13/698,090

(22) PCT Filed: May 18, 2011

(86) PCT No.: PCT/JP2011/002770
§ 371 (c)(1),
(2), (4) Date: Jan. 17, 2013

(87) PCT Pub. No.: WO2011/145343
PCT Pub. Date: Nov. 24, 2011

(65) Prior Publication Data
US 2013/0108710 A1 May 2, 2013

(30) Foreign Application Priority Data
May 19, 2010 (JP) .................................. 2010-115721

(51) Int. Cl.
| A61K 31/197 | (2006.01) |
| A61K 33/26 | (2006.01) |
| A61K 45/06 | (2006.01) |
| A61K 31/221 | (2006.01) |
| A61K 33/06 | (2006.01) |
| A61K 33/30 | (2006.01) |
| A61K 9/48 | (2006.01) |

(52) U.S. Cl.
CPC .............. *A61K 31/197* (2013.01); *A61K 9/4866* (2013.01); *A61K 31/221* (2013.01); *A61K 33/06* (2013.01); *A61K 33/26* (2013.01); *A61K 33/30* (2013.01); *A61K 45/06* (2013.01)

(58) Field of Classification Search
CPC ............................ A61K 31/197; A61K 33/26
See application file for complete search history.

(56) References Cited

U.S. PATENT DOCUMENTS

| 5,955,490 A * | 9/1999 | Kennedy et al. ............... 514/410 |
| 2007/0249721 A1 | 10/2007 | Ito |
| 2009/0123400 A1* | 5/2009 | Lundahl et al. .................. 424/60 |
| 2009/0130227 A1 | 5/2009 | Ito |

FOREIGN PATENT DOCUMENTS

| JP | 2006-124372 | 5/2006 |
| WO | 91/01727 | 2/1991 |
| WO | 99/53962 | 10/1999 |
| WO | 2006/096492 A2 | 9/2006 |

OTHER PUBLICATIONS

Loyevsky M, Lytton SD, Mester B, Libman J, Shanzer A, Cabantchik ZI. "The antimalarial action of desferal involves a direct access route to erythrocytic (*Plasmodium falciparum*) parasites". J Clin Invest. Jan. 1993;91(1):218-24.*
PCT/JP2011/002770; International Preliminary Report on Patentability; Dec. 20, 2012.
Oteiza, Patricia I., et al., "5-Aminolevulinic Acid Induces Iron Release from Ferrition," Archives of Biochemistry and Biophysics (1995) 316/1:607-611.
Smith, Todd G., et al., "Inactivation of *Plasmodium falciparum* by Photodynamic Excitation of Heme-Cycle Intermediates Derived from δ-Aminolevulinic Acid," JID (2004) 190:184.
"Vitamin B12 as a possible antimalarial agent," Vitamin (2008) 82/9:507-512.
Zhang, Shinning, et al., "Heme Mediates Cytotoxicity from Artemisinin and Serves as a General Anti-Proliferation Target," PloS One (2009) 4/10:1-10.
Gorman, Nadia, et al., "Role of Small Differences in CYP1A2 in the Development of Uroporphyria Produced by Iron and 5-Aminolevulinate in C57BL/6 and SWR Strains of Mice," Biochemical Pharmacology (1999) 58:375-382.
Van Hensbroek, Michael Boele, et al., "Iron, but not folic acid, combined with effective antimalarial therapy promotes haematological recovery in African children after acute *falciparum* malaria," Transactions of the Royal Society of Tropical Medicine and Hygiene (1995) 89:672-676.
European Search Report (EP 11783280.8) Dated Oct. 18, 2013.

* cited by examiner

*Primary Examiner* — Ileana Popa
*Assistant Examiner* — Nicole Babson
(74) *Attorney, Agent, or Firm* — Chainey P. Singleton; Edwin S. Flores; Chalker Flores, LLP

(57) ABSTRACT

Provided is an antimalarial drug which is useful for prevention and treatment of infectious diseases caused by malaria parasites. A preventive and/or therapeutic agent for malaria, which contains, as an active ingredient, 5-aminolevulinic acid (ALA), a derivative thereof, or a pharmacologically acceptable salt thereof, is used.

7 Claims, No Drawings

ANTIMALARIAL DRUG WHICH CONTAINS 5-AMINOLEVULINIC ACID OR DERIVATIVE THEREOF AS ACTIVE INGREDIENT

TECHNICAL FIELD

The present invention relates to an antimalarial drug useful for the prevention and treatment of infectious diseases caused by malaria parasites, and more particularly to a preventive agent and a therapeutic agent for malaria containing, as an active ingredient, 5-aminolevulinic acid (ALA) or a derivative thereof.

BACKGROUND ART

Malaria is an infectious disease that is caused by malaria parasites mediated by *anopheles*. Since recorded history, malaria has been the infectious disease most feared by humans mainly in the tropical and subtropical regions. A decrease in the number of malaria-infected people has been temporarily observed because of specific drugs such as quinine and chloroquine. Since the late 1950s, however, drug-resistant parasites have been discovered, and even nowadays, 300 to 500 million people per year are infected with malaria parasites as a reemerging infectious disease. It is said that 1 to 2 million people die from malaria every year. Many other infectious diseases are treated or prevented by vaccination. For example, smallpox was completely eradicated. In the case of malaria, however, since it is an infection caused by parasites, or since the parasites have a complicated life cycle, even a key for the development of a vaccine has not yet been found, although many studies have been conducted. It is said that it may be essentially difficult to develop a vaccine used for malaria.

Many studies have been conducted regarding the development of new drugs or the mechanism of drug resistance. On the other hand, parasites which have developed resistance to drugs have been successively found. Hence, we are facing a crisis. In general, existing antimalarial drugs have strong side effects, and thus these drugs cannot be used in a preventive manner in an area in which malaria is spread. In addition, enormous costs are required for the development of a new drug, and therefore such drug development brings on a serious economic problem.

Conventionally, as a therapeutic method, photodynamic therapy (PDT therapy) has been known. PDT therapy is a treatment method involving combining a photosensitizer with light irradiation. ALA does not have photosensitizing properties by itself. However, since ALA is metabolized to the photosensitizing substance protoporphyrin IX (PPIX) in the body, it is used in the PDT therapy for cancer (see, for example, patent documents 1 to 3). For the PDT therapeutic method using ALA, studies have been conducted on a petri dish using malaria parasites (see, for example, non-patent document 1). PDT therapy certainly exhibited effects on malaria. However, in order for PDT therapy to exhibit some effect by illumination with ordinary indoor light, as much as 2 mM of ALA needs to be added to a medium. It means that at least 20 g of ALA hydrochloride needs to be administered to a person weighing 60 kg, and that it is impossible to administer ALA in such an amount because of a toxicity problem. In order to obtain a sufficient parasiticidal effect when ALA was added to a medium in a concentration of 0.2 mM corresponding to 2 g, that is twice the dosage which general human bodies can tolerate, light irradiation from a strong projector lamp of 410 W for as long as 30 minutes was necessary. These resulted from tests using a transparent medium on a petri dish, and light transmission properties were high. In reality, however, since malaria parasites are parasitic in erythrocytes in the blood, light irradiation is unrealistic, and subsequent studies have not progressed yet.

Moreover, a hair restorer containing ALA and an iron compound as active ingredients (see, for example, patent document 4) and a drug for preventing and/or improving skin roughness (see, for example, patent document 5) have been proposed.

PRIOR ART DOCUMENTS

Patent Documents

Patent Document 1: Japanese Patent No. 2731032
Patent Document 2: Japanese unexamined Patent Application Publication No. 2006-124372
Patent Document 3: Japanese unexamined Patent Application Publication (Translation of PCT Application) No. 2002-512205
Patent Document 4: Japanese Patent No. 3810018
Patent Document 5: Japanese Patent No. 3991063

Non-Patent Documents

Non-patent Document 1: JID (The Journal of Infectious Diseases) 2004: 190, 184-191

SUMMARY OF THE INVENTION

Object to be Solved by the Invention

It has been desired to develop an antimalarial drug having good economic efficiency, which is truly effective and has few side effects, and to which drug-resistant parasites hardly appear. It is an object of the present invention to provide an antimalarial drug useful for the prevention and treatment of malaria, which contains, as an active ingredient, 5-aminolevulinic acid (ALA) or a derivative thereof.

Means to Solve the Object

The present inventors have thoroughly reviewed studies of the life cycle of malaria parasites, the action mechanism of antimalarial drugs including quinine and chloroquine as typical examples, and the resistance of malaria parasites to these antimalarial drugs. As a result, the present inventors have found that malaria parasites are parasitic in erythrocytes and feed on hemoglobin, that the malaria parasites are damaged by heme remaining in the digested hemoglobin, that in order to avoid such damage, the malaria parasites have a capacity to polymerize heme and detoxify the heme to hemozoin, that existing antimalarial drugs inhibits this heme polymerization as their main mechanism of action, and that a drug resistance mechanism is based on promotion of elimination of the drug or detoxification of the drug. To sum up, malaria parasites have a complicated life cycle, and elude even the immune system. However, since malaria parasites feed on hemoglobin, they must approach heme. As a result, malaria parasites are damaged by the heme. This is the greatest disadvantage of malaria parasites.

The present inventors have assumed that ALA that is in a rate-determining step of heme synthesis, or a derivative thereof, might have antimalarial action, directly or mediated by its metabolism intermediate. That is to say, the inventors have thought as follows. ALA, known as a compound having an anemia-improving effect, or a derivative thereof would cause damage to malaria parasites, directly or by being converted to heme. Otherwise, intermediate metabolites such as porphobilinogen (PBG), uroporphyrin, coproporphyrin and protoporphyrin, which are intermediates of heme metabolism, would directly or indirectly cause damage to the parasites, or such intermediate metabolites would act on malaria parasites in a way that suppresses the activity thereof by a method of inhibiting the elimination of existing drugs, and the like.

These ideas belong to a technique using ALA. However, these ideas are completely different from the PDT therapy using the same ALA described in the Background Art, and do not need light irradiation.

ALA, which has been conventionally known as a health food having a variety of health-enhancing effects, was examined as to whether it had an effect on malaria. As a result, it was found that malaria-specific symptoms were immediately suppressed, then fever was suppressed, and even the proliferation of malaria parasites was suppressed. Taking into consideration a high rate of reaction, it is evident that this is a mechanism that is clearly different from the immunostimulation reaction of ALA, which the inventors have already found. As described above, since malaria parasites parasitize erythrocytes by eluding the immune system, the aforementioned effect of ALA on malaria cannot be explained by nature with immunostimulation.

The present inventors have further conducted various studies of an administration method, a combination of the present antimalarial drug with drugs to which malaria parasites have already developed resistance, a dosage, etc., and they have then established a therapeutic agent and a preventive agent for malaria, which comprise ALA as an active ingredient. Thus, the inventors have finally completed the present invention.

Specifically, the present invention relates to:
(1) a preventive and/or therapeutic agent for malaria, which contains, as an active ingredient, 5-aminolevulinic acid (ALA), a derivative thereof, or a pharmacologically acceptable salt thereof;
(2) the preventive and/or therapeutic agent for malaria according to (1) above, wherein ALA or a derivative thereof is a compound represented by the following formula (I):

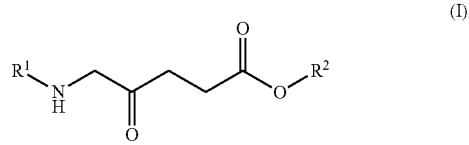

(wherein $R^1$ represents a hydrogen atom or an acyl group, and $R^2$ represents a hydrogen atom, a linear or branched alkyl group, a cycloalkyl group, an aralkyl group, or an aryl group); and
(3) the preventive and/or therapeutic agent for malaria according to (2) above, wherein $R^1$ and $R^2$ each represent a hydrogen atom.

In addition, the present invention relates to:
(4) the preventive and/or therapeutic agent for malaria according to any one of (1) to (3) above, wherein one or more kinds of metal-containing compounds are used in combination; and
(5) the preventive and/or therapeutic agent for malaria according to (4) above, wherein the metal portion of the metal-containing compound is iron, magnesium, or zinc.

Moreover, the present invention relates to:
(6) the preventive and/or therapeutic agent for malaria according to any one of (1) to (5) above, wherein one or more kinds of existing antimalarial drugs are used in combination; and
(7) the preventive and/or therapeutic agent for malaria according to any one of (1) to (6) above, which is used by being administered to an antimalarial-resistant patient.

Furthermore, the present invention relates to:
the ALA according to any one of (1) to (7) above, a derivative thereof, or a pharmacologically acceptable salt thereof, which is used for the prevention and/or treatment of malaria;
use of the ALA according to any one of (1) to (7) above, a derivative thereof, or a pharmacologically acceptable salt thereof, for the prevention and/or treatment of malaria;
use of the ALA according to any one of (1) to (7) above, a derivative thereof, or a pharmacologically acceptable salt thereof, for the production of a medicament for preventing and/or treating malaria;
a method for preventing and/or treating malaria using a pharmaceutical composition containing, as an active ingredient, the ALA according to any one of (1) to (7) above, a derivative thereof, or a pharmacologically acceptable salt thereof; and
a method for preventing and/or treating malaria, which comprises administering a therapeutically effective amount of the ALA according to any one of (1) to (7) above, a derivative thereof, or a pharmacologically acceptable salt thereof.

Effect of the Invention

An antimalarial drug containing the ALA of the present invention as an active ingredient has an excellent effect of treating and/or preventing malaria. Moreover, by using the present antimalarial drug in combination with existing antimalarial drugs, the present antimalarial drug has the effect of enhancing drug efficacy and reducing the dosages of the existing antimalarial drugs, which have strong side effects. The antimalarial drug of the present invention has a mechanism that is completely different from the existing antimalarial drugs, and as for the present antimalarial drug, attention is paid to heme metabolism. Thus, it is considered that malaria parasites hardly develop resistance to the antimalarial drug of the present invention. Furthermore, the combined use of the present antimalarial drug with the existing antimalarial drugs, to which malaria parasites has already developed resistance, can overcome such drug resistance, and can increase the effects of the existing, inexpensive and commonly used antimalarial drugs.

MODE OF CARRYING OUT THE INVENTION

With regard to the definitions of individual groups in a compound represented by the above formula (I) (hereinafter referred to as "compound (I)"), which is used as an antimalarial drug in the present invention, the alkyl group is, for example, linear or branched alkyl containing 1 to 8 carbon atoms. Specific examples include methyl, ethyl, propyl, isopropyl, butyl, isobutyl, sec-butyl, tert-butyl, pentyl, isopentyl, neopentyl, hexyl, heptyl, and octyl.

The cycloalkyl group is cycloalkyl containing 3 to 8 carbon atoms, which optionally has a saturated or partially unsaturated bond. Specific examples include cyclopropyl, cyclobutyl, cyclopentyl, cyclohexyl, cycloheptyl, cyclooctyl, cyclododecyl, and 1-cyclohexenyl.

The aryl portion of the aralkyl group has the same definitions as those of an aryl group as described below, and the alkyl portion thereof has the same definitions of those of the aforementioned alkyl group. The aralkyl group is, for example, aralkyl containing 7 to 15 carbon atoms. Specific examples include benzyl, phenethyl, phenylpropyl, phenylbutyl, benzhydryl, trityl, naphthylmethyl, and naphthylethyl.

The aryl group is, for example, aryl containing 6 to 14 carbon atoms. Specific examples include phenyl, naphthyl, anthryl, and phenanthryl.

The acyl group is a linear or branched alkanoyl group containing 1 to 8 carbon atoms. Specific examples include: formyl, acetyl, propionyl, butyryl, isobutyryl, valeryl, isovaleryl, pivaloyl, hexanoyl, octanoyl and benzylcarbonyl. Alternatively, the acyl group is an aroyl group containing 7 to 14 carbon atoms. Specific examples include: benzoyl, 1-naphthoyl and 2-naphthoyl.

An example of an ALA derivative of the compound (I) used as the antimalarial drug of the present invention is a compound, in which an amino group of ALA is acylated and/or a carboxyl group thereof is esterified. Preferred examples of the ALA derivative include: a compound in which the acyl group is formyl, acetyl, propionyl and butyryl; and a compound in which the ester group is methyl ester, ethyl ester, propyl ester, butyl ester and pentyl ester. Further examples of the ALA derivative include combinations of, formyl and methyl ester, acetyl and methyl ester, propionyl and methyl ester, butyryl and methyl ester, formyl and an ethyl ester group, acetyl and ethyl ester, propionyl and ethyl ester, and butyryl and ethyl ester.

Examples of a pharmacologically acceptable salt of the compound (I) include pharmacologically acceptable acid addition salts, metal salts, ammonium salts and organic amine addition salts. Examples of the acid addition salts include: inorganic acid salts such as hydrochlorides, hydrobromides, hydroiodides, phosphates, nitrates and sulfates; and organic acid addition salts such as formates, acetates, propionates, toluenesulfonates, succinates, oxalates, lactates, tartrates, glycolates, methanesulfonates, butyrates, valerates, citrates, fumarates, maleates and malates. Examples of the metal salts include: alkaline metal salts such as lithium salts, sodium salts and potassium salts; alkaline-earth metal salts such as magnesium and calcium salts; and metal salts such as aluminum and zinc. Examples of the ammonium salts include ammonium salts and alkyl ammonium salts such as tetramethylammonium salts. Examples of the organic amine salts include triethylamine salts, piperidine salts, morpholine salts and toluidine salts.

The compound (I) can be produced by any methods such as chemical synthesis, production using microorganisms and production using enzyme. For example, an acyl group in the amino group of the ALA derivative, an ester group in the carboxyl group of the ALA derivative can be produced by performing acylation of the amino group, esterification of the carboxyl group, and the like, according to ordinary chemical synthetic methods.

When the salt of the compound (I) is to be obtained, if the compound (I) is obtained in the form of a salt, it may be directly purified. On the other hand, if the compound (I) is obtained in a free form, it may be dissolved or suspended in a suitable organic solvent, an acid or a base may be then added to the solvent, and a salt may be formed by an ordinary method.

The compound (I) and a pharmacologically acceptable salt thereof may be present in the form of an addition product with water or various solvents. These addition products can also be used as the antimalarial drugs of the present invention.

The compound (I) usable as the antimalarial drug of the present invention is not particularly limited, as long as it is a compound (I). The compounds (I) can be used singly or in combinations of two or more (I) as appropriate. Desirable examples of the compounds (I) include: ALA; various esters thereof, such as methyl ester, ethyl ester, propyl ester, butyl ester and pentyl ester; and their hydrochloride, phosphate and nitrate. Examples of the most desirable compound include the hydrochloride of ALA and the phosphate of ALA.

In addition, in the present invention, a metal-containing compound can be used in combination with the compound (I). Such a metal-containing compound can be used in a range that does not cause an excess symptom. For example, such a metal-containing compound is used in combination in an amount of 0.1 to 10 (w/w) times, preferably 0.5 to 5 (w/w) times, and more preferably 0.8 to 2 (w/w) times the amount of the compound (I).

Preferred examples of a metal portion of the metal-containing compound include iron, magnesium, zinc, nickel, vanadium and cobalt. Among these, metals involved in the biosynthesis of porphyrin or heme, such as iron, magnesium and zinc, are more preferable. These metal-containing compounds are not particularly limited, as long as these are compounds containing the aforementioned metal in a molecule thereof and they do not cause any adverse effect on the present invention. Examples of a compound containing iron in a molecule thereof include ferrous citrate, ferric sodium citrate, ferric ammonium citrate, ferric pyrophosphate, heme iron, dextran iron, ferrous lactate, ferrous gluconate, sodium diethylenetriaminepentaacetate, ammonium diethylenetriaminepentaacetate, sodium ethylenediaminetetraacetate, ammonium ethylenediaminepentaacetate, iron triethylenetetramine, iron sodium dicarboxymethylglutamate, iron ammonium dicarboxymethylglutamate, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron sodium succinate citrate, iron sulfate and ferrous glycine sulfate. Among these, ferrous citrate and iron sodium citrate are preferable.

Preferred examples of a compound containing magnesium in a molecule thereof include magnesium citrate, magnesium benzoate, magnesium acetate, magnesium oxide, magnesium chloride, magnesium hydroxide, magnesium carbonate, magnesium sulfate, magnesium silicate, magnesium nitrate, magnesium diammonium diethylenetriaminepentaacetate, magnesium disodium ethylenediaminetetraacetate and magnesium protoporphyrin.

Preferred examples of a compound containing zinc in a molecule thereof include zinc chloride, zinc oxide, zinc nitrate, zinc carbonate, zinc sulfate, zinc diammonium diethylenetriamine pentaacetate, zinc disodium ethylenediaminetetraacetate, zinc protoporphyrin and zinc-containing yeast.

These metal-containing compounds may be used singly or in combinations of two or more. These metal-containing compounds may be administered, simultaneously with the compound (I) or separately. The dosage form or administration method of the metal-containing compound may be the same as those of the compound (I), or may be different from those of the compound (I).

Moreover, in the present invention, existing antimalarial drugs can be used in combination with the compound (I). The existing antimalarial drugs used in combination with the compound (I) are not particularly limited. Examples of such existing antimalarial drugs include quinine, chloroquine, mefloquine, sulfadoxine, pyrimethamine, atovaquone, proguanil, artemether, lumefantrine, artesunate, primaquine and artemisinin. In particular, chloroquine, mefloquine, sulfadoxine, pyrimethamine and the like are inexpensive antimalarial drugs, which have long been used. However, it is known that there are many drug-resistant parasites which have developed resistance thereto. Thus, it would be significantly meaningful, if the resistance of the parasites to these drugs were canceled by the combined use of the compound (I) with them. An additive effect, or in some cases, a synergistic effect can be anticipated. These antimalarial drugs may be used singly or in combinations of two or more. These antimalarial drugs may be administered, simultaneously with the compound (I) or separately. The dosage form or administration method of these antimalarial drugs may be the same as those of the compound (I), or may be different from those of the compound (I).

Furthermore, in the present invention, the compound (I) can be used by being administered to a malaria patient, and especially to a malaria patient who has obtained resistance to existing antimalarial drugs, by a single use thereof or by a combined use with the existing antimalarial drugs.

The compound (I) or a pharmacologically acceptable salt thereof can be administered alone to a malaria patient. However, as necessary, other ingredients such as other medicinal ingredients and nutrients may be added to the compound (I) or a pharmacologically acceptable salt thereof. In general, it is desired to produce various pharmaceutical preparations. Such a pharmaceutical preparation can be produced by mixing an active ingredient with one or more pharmacologically acceptable carriers according to an ordinary pharmaceutical method. As a carrier that can be blended with the compound (I) or a pharmacologically acceptable salt thereof, an organic or inorganic, solid or liquid, pharmacologically acceptable carrier material, which is suitable for administration and is generally inactive, can be used. Specific examples of such a carrier include crystalline cellulose, gelatin, lactose, starch, magnesium stearate, talc, vegetable or animal fat and oil, gum and polyalkylene glycol.

Examples of administration routes include oral administration including sublingual administration, inhalation administration, intravenous administration including drip infusion, transdermal administration using a poultice and the like, and parenteral administration such as a suppository.

Examples of dosage forms include an injection, a drop, a tablet, a capsule, a granule, a syrup, a poultice, and a suppository. These preparations can be produced using a solvent, a disperser, a thickener, an excipient, etc., as appropriate, according to an ordinary method.

For example, an injection may be produced by adding water, a saline, vegetable oil, a solubilizer a preservative or the like according to an ordinary method. A tablet may be produced by mixing various additives such as lactose, starch, magnesium stearate, hydroxypropyl cellulose, polyvinyl alcohol, a surfactant and glycerin according to an ordinary method. An inhalant may be produced by adding, for example, lactose according to an ordinary method. When these preparations are prepared in the form of an aqueous solution, attention should be paid not to convert the aqueous solution to an alkaline solution in order to prevent decomposition of the compound (I). If the aqueous solution is converted to an alkaline solution, decomposition of the active ingredient can be prevented by removing oxygen.

The effective amount and the number of administration of the compound (I) or a pharmacologically acceptable salt thereof are different depending on the dosage form thereof, and the age, body weight, symptoms, etc. of a patient. The total amount of the compound (I) comprised in the preparation may be generally 1 mg to 3000 mg, desirably 3 mg to 1000 mg, and more desirably 10 mg to 700 mg, per adult, relative to the number of moles of ALA hydrochloride. The administration period is not particularly limited, and the compound (I) can be administered to a patient either in the morning or in the evening. The compound (I) is preferably administered once a day, or divided over several administrations per day when the dosage is high. The number of days in which the compound (I) is administered to a patient is different depending on symptoms. Since malaria is characterized in that its symptoms appear intermittently, it is desirable that the compound (I) be continuously administered to a patient for 3 to 4 days even after alleviation of the symptoms.

The present invention will be more specifically described in the following examples. However, these examples are not intended to limit the technical scope of the present invention.

EXAMPLE 1

A single capsule comprising 50 mg of ALA phosphate and 57.36 mg of sodium ferrous citrate, which had been produced in Preparation Example 1, was orally administered to each of five patients infected with malaria (two patients of 8 years old, and three patients each of 9, 10 or 12 years old) under the supervision of a doctor. One or two hours after the administration, symptoms such as headache, vertigo, nausea and malaise were reduced in all of the patients. Such an improvement that the children who had stayed limply began to play was also observed. Moreover, two or three hours after the administration, fever was improved, and six hours later, fever went down. It is to be noted that the presence of malaria parasites was confirmed in blood test performed before administration of the capsule.

A single capsule of the same capsule as described above was administered to all of the patients once a day, and on the $5^{th}$ day, their blood was examined again. As a result, the presence of malaria parasites was still confirmed, although the number of parasites decreased. During this period, malaria symptoms including fever did not reappear. For further two days, the same capsule as described above was administered to the patients, and thereafter, administration was suspended. However, malaria symptoms did not appear. Since the symptoms completely disappeared, it was considered that the patients were cured, and a blood test after cure was not carried out.

From the results of the present example, it was found that ALA is effective for the treatment of malaria.

EXAMPLE 2

A single capsule comprising 250 mg of ALA hydrochloride, which had been produced in Preparation Example 2, was administered to a 24-year-old male patient who was infected with malaria parasites and had high fever. One hour after the administration, symptoms such as headache, vertigo, nausea and malaise were improved. Two hours later, fever was decreased, and one day later, the symptoms completely disappeared. Thereafter, a single capsule of the same capsule as described above was administered to the patient once a day for 3 days. As a result, malaria symptoms did not reappear. The body temperature of the patient was rather lower than his normal body temperature by approximately 0.5 degrees. In a test of malaria parasites performed on day 3, the presence of the parasites was confirmed, but the number of them did not increase. From these results, it became clear that ALA is effective for the treatment of malaria.

EXAMPLE 3

A predetermined amount of chloroquine was administered to a 32-year-old male patient who developed malaria. However, sufficient effects could not be obtained probably because of drug resistance. He suffered from headache, vertigo and nausea, and his body temperature was kept around 38 degrees. While administering chloroquine, a single capsule of the same capsule as used in Example 1 was also administered to the patient once a day. As a result, the symptoms were improved in about half a day. After administration of the capsule for 3 days, administration was suspended. However, the symptoms did not reappear.

These results suggest that ALA effectively acted on the treatment of malaria by directly acting on chloroquine-resistant malaria parasites or by removing the drug resistance of the malaria parasites.

EXAMPLE 4

A single capsule comprising 25 mg of ALA phosphate and 28.68 mg of sodium ferrous citrate, which had been produced in Preparation Example 3, was administered every day to each of ten persons who were working in areas severely contaminated by malaria. They worked under unprotected conditions for 1 month, but none of them became infected with malaria during this period. On an empirical basis, about half of people working under such conditions would become infected with malaria. Thus, it is considered that administration of ALA preventively acted on malaria infection.

EXAMPLE 5

An iron (II) chloride aqueous solution was added to 1 ml of *Plasmodium falciparum* 3D7 culture medium having an infection rate of 0.3% to a final concentration of 0.1, 1, 10, and 100 µM. As a control, a culture medium to which sterilized water had been added was used. Three culture media were prepared for each of the aforementioned concentrations, and a 12-well plate was used. After each culture medium had been cultured for 48 hours, the infection rate was measured by Giemsa staining. In addition, as for an ALA-added medium, an ALA chloride aqueous solution was added to the medium to a final concentration of 200 µM, and an iron (II) chloride aqueous solution was then added thereto to a final concentration of 0.1, 1, 10, and 100 µM. As described above, the culture medium was cultured for 48 hours, and the infection rate was then measured by Giemsa staining.

The infection (proliferation) rate (%) was calculated using the following formula:

[(Infection rate after 48 hours–infection rate at initiation of culture)/(infection rate of control after 48 hours–infection rate at initiation of culture)]× 100.

It is to be noted that the infection rate at initiation of the culture was set at 0.3%.

The ratio of an increase in the infection rate caused by culture was indicated by setting a region to which neither iron nor ALA was added at 100%. The results are shown in Table 1.

Infection rate (%) by Random Culture

| Infection rate (%) by random culture | | | | | |
|---|---|---|---|---|---|
| | 0 | 0.1 µM | 1 µM | 10 µM | 100 µM |
| Without ALA | 100 | 98 | 97 | 95 | 82 |
| With ALA | 96 | 88 | 86 | 59 | 57 |

As is apparent from Table 1, it was found that ALA has the effect of suppressing a malaria infection rate, and that a combination of ALA and a metal-containing compound increases the aforementioned effect, but a single use of the metal-containing compound does not have such an effect. It is found that the effect on the subjects shown in Examples 1 to 4 is a reduction in the malaria parasite infection rate.

EXAMPLE 6

According to a common method, there was prepared a *Plasmodium falciparum* 3D7 culture medium having an infection rate of 0.3%, which was subjected to synchronized culture at the ring stage by treating with 5% sorbitol. The infection rate was measured by the same method as that described in Example 5. The final concentration of ALA hydrochloride was set at 200 µM. The results are shown in Table 2.

| Infection rate by synchronized culture (ring stage) | | | | | |
|---|---|---|---|---|---|
| | 0 | 0.1 µM | 1 µM | 10 µM | 100 µM |
| With ALA | 95 | 69 | 58 | 51 | 5 |

As is apparent from Table 2, it is found that ALA is effective for suppression of malaria infection, and that a combination of ALA and a metal-containing compound significantly increases the aforementioned effect. Moreover, from a comparison with Example 5, it is found that the infection rate-suppressing effect of ALA, or ALA and a metal-containing compound, is particularly remarkable at the ring stage. If malaria parasites can be suppressed at the ring stage, they cannot transfer to the trophozoite stage. Thus, if ALA is continuously administered to a patient, the patient will be able to escape from malaria infection. These findings match the observation results in Examples 1 to 4.

EXAMPLE 7

A culture medium was prepared in the same manner as in Example 5 with the exception that 2 ml of a culture medium having an infection rate of 2% was used. To the thus prepared culture medium, iron(II) chloride (final concentration: 10 µM) and ALA hydrochloride (final concentration: 200 µM) were added, followed by culture for 8 hours. Thereafter, the infection rate was measured by Giemsa staining. As a result, the infection rate was found to be 0.47%. On the other hand, the infection rate of a system to which nothing had been added was found to be 3.1%. These results demonstrated that a combination of ALA and a metal-containing compound is effective for suppression of malaria infection, even in a case in which the infection rate is high.

EXAMPLE 8

ALA hydrochloride was added to a final concentration of 200 µM to a culture medium that had been prepared in the same manner as in Example 7. The obtained mixture was cultured for 8 hours, and thereafter, irradiated with white LED for 15 minutes. The resultant was further cultured for 8 hours, and the infection rate was then measured by Giemsa staining. As a result, the infection rate was found to be 1.8%. These results demonstrated that ALA is effective for suppression of malaria infection, even in a case in which the infection rate is high.

PREPARATION EXAMPLE 1

A preparation is prepared from a composition consisting of 50.0 mg of ALA phosphate, 57.36 mg of sodium ferrous citrate, 150 mg of pregelatinized starch, and 2.5 mg of silicon dioxide, using a hard capsule of No. 2 according to an ordinary method.

PREPARATION EXAMPLE 2

A hard capsule containing 250 mg of ALA hydrochloride is prepared according to an ordinary method.

PREPARATION EXAMPLE 3

A preparation is prepared from a composition consisting of 25.0 mg of ALA phosphate, 28.68 mg of sodium ferrous citrate, 204 mg of pregelatinized starch, and 2.5 mg of silicon dioxide, using a hard capsule of No. 2 according to an ordinary method.

INDUSTRIAL APPLICABILITY

The antimalarial drug of the present invention containing ALA as an active ingredient can be used as a therapeutic and/or preventive agent for malaria. Moreover, by using the present antimalarial drug in combination with existing antimalarial drugs, the drug efficacy can be enhanced, or the amounts of the existing antimalarial drugs used, which have strong side effects, can be reduced. The combined use of the antimalarial drug of the present invention with the existing antimalarial drugs, to which malaria has developed resistance, can overcome such drug resistance, and can increase the effects of the existing, inexpensive and commonly used antimalarial drugs.

The invention claimed is:

1. A method for treating or preventing malaria in a subject without performing light irradiation comprising the steps of:
   identifying a subject suspected of having malaria; and
   administering a therapeutically effective amount of a compound represented by the following formula (I) or a pharmacologically acceptable salt thereof,

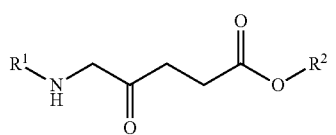

(I)

wherein $R^1$ represents a hydrogen atom or an acyl group, and $R^2$ represents a hydrogen atom, a linear or branched alkyl group, a cycloalkyl group, an aralkyl group, or an aryl group; in combination with one or more kinds of metal-containing compounds, wherein the metal portion of the metal-containing compound is iron, magnesium, or zinc.

2. The method of claim 1, comprising administering a therapeutically effective amount of the compound represented by formula (I) or a pharmacologically acceptable salt thereof in combination with one or more kinds of metal-containing compounds, wherein the metal portion of the metal-containing compound is iron, magnesium, or zinc, and further in combination with one or more kinds of known antimalarial drugs.

3. The method of claim 1, comprising administering a therapeutically effective amount of the compound represented by formula (I) or a pharmacologically acceptable salt thereof in combination with one or more kinds of metal-containing compounds, wherein the metal portion of the metal-containing compound is iron, magnesium, or zinc to an antimalarial drug-resistant patient.

4. The method of claim 2, comprising administering a therapeutically effective amount of the compound represented by formula (I) or a pharmacologically acceptable salt thereof in combination with one or more kinds of metal-containing compounds, wherein the metal portion of the metal-containing compound is iron, magnesium, or zinc and further in combination with one or more kinds of known antimalarial drugs to an antimalarial drug-resistant patient.

5. The method of claim 1, wherein $R^1$ and $R^2$ each represent a hydrogen atom.

6. The method of claim 1, comprising administering a therapeutically effective amount of the compound represented by formula (I) or a pharmacologically acceptable salt thereof wherein $R^1$ and $R^2$ each represent a hydrogen atom, in combination with one or more kinds of metal-containing compounds, wherein the metal portion of the metal-containing compound is iron, magnesium, or zinc, and further in combination with one or more kinds of known antimalarial drugs.

7. The method of claim 1, comprising administering a therapeutically effective amount of the compound represented by formula (I) or a pharmacologically acceptable salt thereof wherein $R^1$ and $R^2$ each represent a hydrogen atom, in combination with one or more kinds of metal-containing compounds, wherein the metal portion of the metal-containing compound is iron, magnesium, or zinc to an antimalarial drug-resistant patient.

* * * * *